(12) United States Patent
Taoka et al.

(10) Patent No.: US 10,149,916 B2
(45) Date of Patent: Dec. 11, 2018

(54) ION SPRAYING APPARATUS, ION SPRAYING SYSTEM, AND ION SPRAYING METHOD

(71) Applicant: Panasonic Intellectual Property Management Co., Ltd., Osaka (JP)

(72) Inventors: Hiroki Taoka, Kyoto (JP); Hiroyuki Kayama, Osaka (JP); Ichiro Takei, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 27 days.

(21) Appl. No.: 14/667,446

(22) Filed: Mar. 24, 2015

(65) Prior Publication Data
US 2015/0290348 A1    Oct. 15, 2015

(30) Foreign Application Priority Data

Apr. 9, 2014    (JP) ................. 2014-080459

(51) Int. Cl.
*A61L 2/14*    (2006.01)
*A61L 9/22*    (2006.01)
(Continued)

(52) U.S. Cl.
CPC ............. *A61L 2/14* (2013.01); *A61L 9/22* (2013.01); *B64C 39/024* (2013.01);
(Continued)

(58) Field of Classification Search
CPC .......... A61L 2/14; A61L 9/22; G05D 1/0011; G05D 1/102; B64C 39/024
See application file for complete search history.

(56) References Cited

U.S. PATENT DOCUMENTS 4,993,913 A  * 2/1991  Ohtsuki ............... B25J 5/00
                                              180/901
6,459,955 B1 * 10/2002 Bartsch ............... A47L 9/00
                                              318/568.11
(Continued)

FOREIGN PATENT DOCUMENTS

JP    2010-075609    4/2010
JP    2013-242738    12/2013
(Continued)

OTHER PUBLICATIONS

Extended European Search Report dated Aug. 17, 2015 for European Patent Application No. 15155858.2.

*Primary Examiner* — Regina M Yoo
(74) *Attorney, Agent, or Firm* — Greenblum & Bernstein, P.L.C.

(57) ABSTRACT

A communication unit receives spraying target information indicating a spray target. A spraying target detector detects the spray target indicated in the spraying target information in space. A spray control unit is a unit that performs ion-spraying processing on the spray target at a predetermined frequency. In the ion-spraying processing, the spray control unit determines a moving direction of an ion spraying apparatus from a current location to the detected spray target, and sprays ions on the spray target when a distance between the spray target and the ion spraying apparatus is within a first threshold value. A flight control unit controls a flight of the ion spraying apparatus in the moving direction.

5 Claims, 5 Drawing Sheets

(51) Int. Cl.
*B64C 39/02* (2006.01)
*G05D 1/00* (2006.01)

(52) U.S. Cl.
CPC ........ *G05D 1/0094* (2013.01); *A61L 2202/16* (2013.01); *B64C 2201/027* (2013.01); *B64C 2201/108* (2013.01); *B64C 2201/12* (2013.01); *B64C 2201/141* (2013.01)

(56) References Cited

U.S. PATENT DOCUMENTS

| | | | | |
|---|---|---|---|---|
| 6,496,754 | B2 * | 12/2002 | Song | A47L 9/009 318/568.12 |
| 6,588,701 | B2 * | 7/2003 | Yavnai | G05D 1/0038 244/12.1 |
| 6,597,143 | B2 * | 7/2003 | Song | A47L 9/009 15/323 |
| 6,611,120 | B2 * | 8/2003 | Song | G05D 1/0038 318/568.12 |
| 6,712,312 | B1 * | 3/2004 | Kucik | B64C 39/024 244/1 R |
| 6,815,918 | B2 * | 11/2004 | Porat | E04H 4/1654 15/1.7 |
| 7,166,983 | B2 * | 1/2007 | Jung | G05D 1/0225 180/167 |
| 7,227,327 | B2 * | 6/2007 | Im | G05D 1/0225 318/568.12 |
| 7,233,122 | B2 * | 6/2007 | Kim | A47L 9/009 318/568.12 |
| 7,805,220 | B2 * | 9/2010 | Taylor | G05D 1/0219 318/568.12 |
| 2008/0023589 | A1 | 1/2008 | Miles et al. | |
| 2013/0008998 | A1 * | 1/2013 | Morris | B64C 27/02 244/3 |
| 2013/0068892 | A1 * | 3/2013 | Bin Desa | B64C 39/024 244/190 |
| 2013/0175405 | A1 | 7/2013 | Khozikov et al. | |
| 2014/0230179 | A1 | 8/2014 | Matsubara et al. | |
| 2014/0303814 | A1 * | 10/2014 | Burema | A01B 79/005 701/3 |

FOREIGN PATENT DOCUMENTS

| | | |
|---|---|---|
| WO | 20131051365 | 4/2013 |
| WO | 20131175839 | 11/2013 |

* cited by examiner

ION SPRAYING APPARATUS, ION SPRAYING SYSTEM, AND ION SPRAYING METHOD

BACKGROUND

1. Technical Field

The present disclosure relates to an ion spraying apparatus, an ion spraying system, and an ion spraying method.

2. Description of the Related Art

In recent years, techniques for maintaining a sanitary environment have received widespread attention, such as sterilization, disinfection, or deodorization. For example, Patent Literature 1 discloses production of highly concentrated ions (microparticle ions) generated from moisture in an atmosphere to achieve sterilization, disinfection, or deodorization. For example, in a device that includes a needle-shaped discharge electrode and a Peltier device for cooling the needle-shaped discharge electrode to cause water condensation on the needle-shaped discharge electrode, nanoe (registered trademark), which is one type of the above-described ions, is produced by application of a high voltage on the needle-shaped discharge electrode.

Patent Literature 2 discloses a technique to provide a self-propelled cleaner that cleans a floor surface with a sensor capable of inspecting air quality, to cause the cleaner to remain at a position at which an abnormality is detected, such as an abnormal odor concentration, and to generate highly concentrated ions.

CITATION LIST

Patent Literatures

PTL 1: Unexamined Japanese Patent Publication No. 2010-75609

PTL 2: Unexamined Japanese Patent Publication No. 2013-081604

SUMMARY

Generally, effects including sterilization by ions, such as nanoe, decrease rapidly as ions diffuse. That is, ions need to be sprayed on a spray target from closet range as much as possible. However, it takes time and effort for a person to perform ion-spraying from close range on the spray target manually each time. In addition, a failure to spray ions inhibits the effects from lasting, such as sterilization in the spray target.

Although the technique disclosed in Patent Literature 2 checks an abnormality in air quality, the technique cannot address a source of the air quality abnormality. A failure to address the source inhibits reduction in influence on a person.

One non-limiting and exemplary aspect of the present disclosure is an ion spraying apparatus that sprays ions on a spray target from an optimal distance at a predetermined frequency, to allow the effects of sterilization, disinfection, or deodorization to last in the spray target.

Additional benefits and advantages of one aspect of the present disclosure will be apparent from the present specification and the drawings. The benefits and/or advantages may be individually provided by various aspects and features disclosed in the present specification and the drawings, which need not all be provided in order to obtain one or more of such benefits and/or advantages.

The ion spraying apparatus according to one aspect of the present disclosure includes a receiver that receives spraying target information indicating a spray target, a spraying target detector that detects the spray target, a spray controller that has the ion spraying apparatus move toward the detected spray target and to perform ion-spraying when a distance between the spray target and the ion spraying apparatus is within a first threshold value, and a flight controller that controls a flight of the ion spraying apparatus.

These comprehensive or specific aspects may be implemented by a system, a method, an integrated circuit, a computer program, or a computer-readable recording medium, and may be implemented by an arbitrary combination of an apparatus, a system, a method, an integrated circuit, a computer program, and a computer-readable recording medium. The computer-readable recording medium includes a nonvolatile recording medium such as a CD-ROM (Compact Disc-Read Only Memory).

According to the present disclosure, it is possible to perform ion-spraying on the spray target from an optimal distance at a predetermined frequency, and to allow effects of sterilization, disinfection, or deodorization to last in the spray target.

DETAILED DESCRIPTION

Exemplary embodiments of the present disclosure will be described in detail below with reference to the drawings.

First Exemplary Embodiment

Figure 1A:
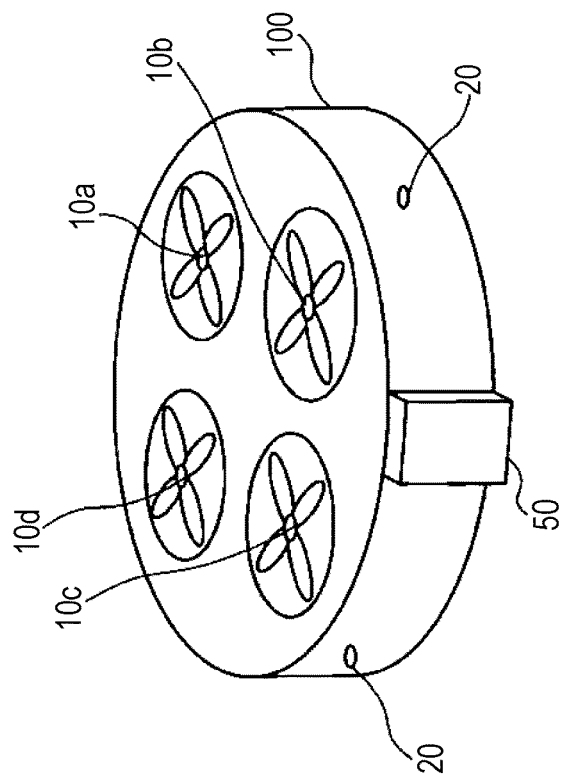
FIG. 1A and FIG. 1B are perspective views each illustrating an ion spraying apparatus according to a first exemplary embodiment of the present disclosure.
Figure 1B:
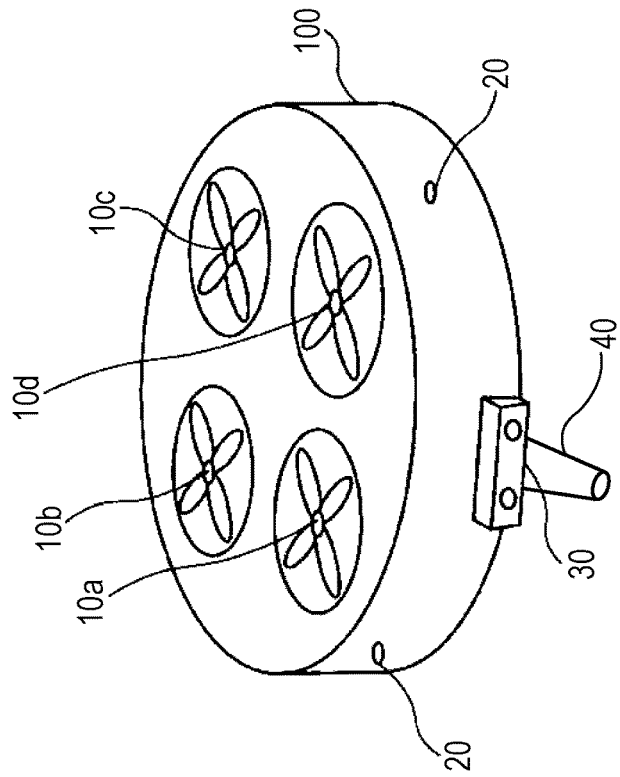

FIG. 1A illustrates a perspective view of ion spraying apparatus 100 according to the present exemplary embodiment. FIG. 1B is a perspective view of ion spraying apparatus 100 of FIG. 1A viewed from an opposite direction.

As illustrated in FIG. 1A and FIG. 1B, ion spraying apparatus 100 includes propellers 10a to 10d, ultrasonic sensors 20, compound eye camera 30, spraying unit 40, and GPS (Global Positioning System) receiver 50.

Four thrust propellers 10a to 10d are driven by, for example, an ultrasonic motor (not illustrated). The ultrasonic motor controls a number of rotations of respective propellers 10a to 10d, thereby enabling ion spraying apparatus 100 to fly in vertical and horizontal directions. A number of propellers included in ion spraying apparatus 100 is not limited to four.

Ion spraying apparatus 100 uses respective ultrasonic sensors 20, compound eye camera 30, or GPS receiver 50 to recognize a location of ion spraying apparatus 100, and to control a flight of ion spraying apparatus 100 to avoid a collision with an obstacle (such as a ceiling, a wall, and a household utensil (furniture)) in space (for example, inside a room). Ion spraying apparatus 100 uses respective ultrasonic sensors 20, compound eye camera 30, or GPS receiver 50 to recognize a spray target to be sprayed with ions, and to control the flight of ion spraying apparatus 100 to move to a position optimal for spraying ions on the spray target. Ultrasonic sensors 20, compound eye camera 30, and GPS receiver 50 may be installed not only on a side of ion spraying apparatus 100 as illustrated in FIG. 1A and FIG. 1B, but also in an upper or lower part of ion spraying apparatus 100.

Spraying unit 40 sprays ions (for example, nanoe) generated by an ion generating apparatus (not illustrated).

In addition, ion spraying apparatus 100 may include an antenna (not illustrated in FIG. 1) for performing communication with a control device such as a server, or with a device appliance retained by a person. For example, ion spraying apparatus 100 receives spraying target information (such as image information or location information) that specifies the spray target via the antenna, detects the spray target indicated in the received spraying target information, and sprays ions on the spray target.

[Configuration of Ion Spraying Apparatus 100]

Figure 2:
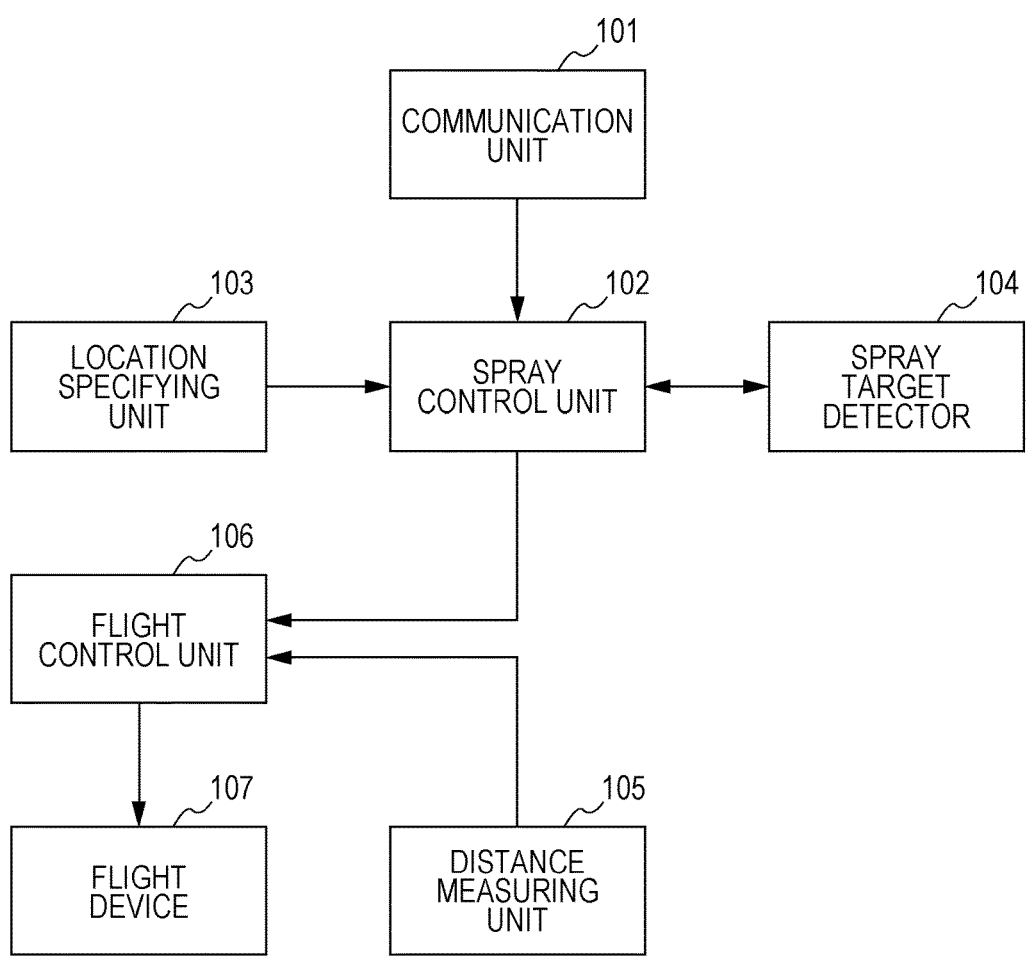
FIG. 2 is a block diagram illustrating a configuration of the ion spraying apparatus according to the first exemplary embodiment of the present disclosure.

FIG. 2 is a block diagram illustrating a configuration of ion spraying apparatus 100 according to the present exemplary embodiment. Ion spraying apparatus 100 illustrated in FIG. 2 includes communication unit 101, spray control unit 102, location specifying unit 103, spraying target detector 104, distance measuring unit 105, flight control unit 106, and flight device 107.

Communication unit 101 receives the spraying target information (image information or location information) that specifies the spray target by ion spraying apparatus 100, and outputs the spraying target information to spray control unit 102. Examples of the spray target include an object that serves as a source of contact infection, such as a doorknob, a remote control, and a keyboard. For example, the spraying target information may be registered in ion spraying apparatus 100 through operational input of a person, and may be downloaded into ion spraying apparatus 100 as information accumulated in a server.

Spray control unit 102 controls ion (for example, nanoe) spraying on the spray target indicated in the spraying target information received from communication unit 101.

Specifically, spray control unit 102 receives location information that indicates a current location of ion spraying apparatus 100 from location specifying unit 103. Spray control unit 102 instructs spraying target detector 104 to detect the spray target in space (room) in which ion spraying apparatus 100 can fly, based on the spraying target information. Spray control unit 102 then determines a moving direction from the current location of ion spraying apparatus 100 to the spray target based on the location information about the spray target in the space received from spraying target detector 104. Spray control unit 102 then instructs flight control unit 106 to move ion spraying apparatus 100 in the determined moving direction. That is, ion spraying apparatus 100 approaches the spray target while spraying target detector 104 is detecting (measuring a distance from) the spray target. Spray control unit 102 then sprays ions on the spray target from spraying unit 40 illustrated in FIG. 1 when ion spraying apparatus 100 reaches the spray target. For example, spray control unit 102 determines that ion spraying apparatus 100 has reached the spray target when the distance between ion spraying apparatus 100 and the spray target is within a predetermined threshold value, In addition, spray control unit 102 sprays ions on the spray target at a predetermined frequency. For example, spray control unit 102 sprays ions on the spray target periodically at preset time intervals. In addition, spray control unit 102 may spray ions on the spray target in response to a request from a person.

Spray control unit 102 may, for example, use data acquired from an instrument such as compound eye camera 30 or GPS receiver 50 to recognize a structure (location of a ceiling, a wall, and a household utensil) of the space (room) in which ion spraying apparatus 100 can fly, and may create a three-dimensional map that shows the structure of the space. Spray control unit 102 may then recognize the location of ion spraying apparatus 100 and the location of the spray target in the created three-dimensional map to determine the moving direction of ion spraying apparatus 100.

Location specifying unit 103 specifies the current location of ion spraying apparatus 100 to output the specified location information to spray control unit 102. Location specifying unit 103 acquires, for example, location data (latitude, longitude) on ion spraying apparatus 100 received from GPS receiver 50 illustrated in FIG. 1. In addition, location specifying unit 103 may include, for example, a gyro sensor (not illustrated), detect a motion (behavior) of ion spraying apparatus 100, and correct the location data based on a detection result.

Spraying target detector 104 detects the spray target in the space in which ion spraying apparatus 100 flies, the spray target being indicated in the spraying target information received from spray control unit 102. For example, spraying target detector 104 may perform image recognition processing using an image acquired from compound eye camera 30 illustrated in FIG. 1 to detect an object that corresponds to an image of the spray target indicated in the spraying target information, and may output the location information (such as a direction or a distance) about the detected spray target to spray control unit 102. Alternatively, spraying target detector 104 may detect the direction and distance of the spray target from the location data (current location of ion spraying apparatus 100) acquired from GPS receiver 50 illustrated in FIG. 1 and the location data on the spray target indicated in the spraying target information. Spray control unit 102 outputs the detected location information about the spray target (such as a direction, a distance, or latitude/longitude) to spray control unit 102.

Distance measuring unit 105 measures a distance between the obstacle (such as a wall or a household utensil) to ion spraying apparatus 100 and ion spraying apparatus 100, and outputs a measurement result to flight controller 106. Distance measuring unit 105 measures the distance from the obstacle by using, for example, information acquired from ultrasonic sensors 20 or compound eye camera 30 illustrated in FIGS. 1A and 1B.

Flight controller 106 controls a flight (movement) of ion spraying apparatus 100 in the moving direction instructed from spray control unit 102. In addition, flight controller 106 controls the flight (movement) of ion spraying apparatus 100 based on a distance measuring result received from distance measuring unit 105 to avoid a collision between ion spraying apparatus 100 and the obstacle.

Flight device 107 causes ion spraying apparatus 100 to fly in accordance with control from flight controller 106. Flight device 107 is, for example, propellers 10a to 10d illustrated in FIGS. 1A and 1B, and the ultrasonic motor that is not illustrated.

[Operation of Ion Spraying Apparatus 100]

An operation of ion spraying apparatus 100 thus configured will be described.

Figure 3:
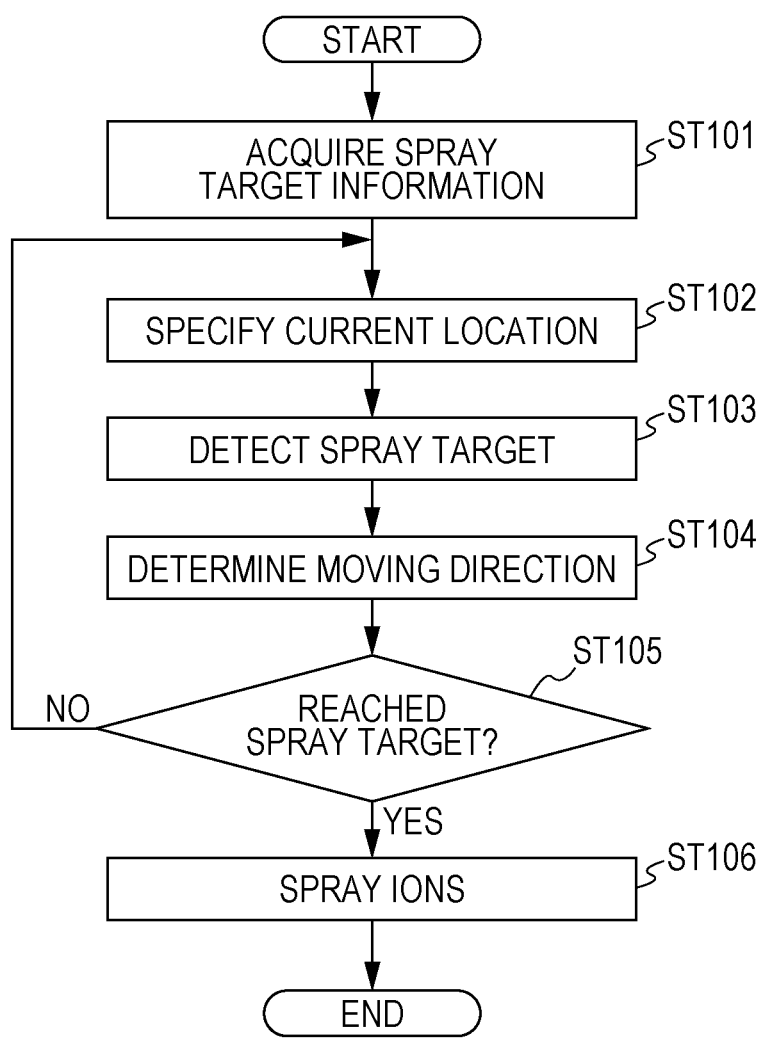
FIG. 3 is a flow chart illustrating an operation of the ion spraying apparatus according to the first exemplary embodiment of the present disclosure.

FIG. 3 is a flow chart illustrating a flow of spraying processing in ion spraying apparatus 100.

In FIG. 3, ion spraying apparatus 100 acquires the spraying target information that specifies the spray target in step (hereinafter represented as "ST") 101.

In ST102, ion spraying apparatus 100 specifies the current location of ion spraying apparatus 100. In ST103, ion spraying apparatus 100 detects, in the space, the spray target indicated in the spraying target information acquired in ST101.

In ST104, ion spraying apparatus 100 determines the moving direction of ion spraying apparatus 100 based on the current location of ion spraying apparatus 100 specified in ST102, and on the location of the spray target detected in ST103. Based on the moving direction determined in ST104, ion spraying apparatus 100 flies toward the location of the spray target.

In ST105, ion spraying apparatus 100 determines whether ion spraying apparatus 100 has reached the location of the spray target. Specifically, ion spraying apparatus 100 (spray control unit 102) determines whether the distance between the spray target and ion spraying apparatus 100 (for example, spraying unit 40 illustrated in FIG. 1) is a distance optimal for spraying ions. For example, ion spraying apparatus 100 may determine that the distance is optimal for spraying ions when the distance between the spray target and ion spraying apparatus 100 (spraying unit 40) is within a predetermined threshold value.

When ion spraying apparatus 100 has not reached the location of the spray target (ST105:No), ion spraying apparatus 100 returns to processing of ST102. That is, ion spraying apparatus 100 approaches the spray target by repeating processing of ST102 to ST104 until ion spraying apparatus 100 reaches the location (optimal location for spraying) of the spray target.

When ion spraying apparatus 100 reaches the location of the spray target (ST105:Yes), ion spraying apparatus 100 sprays ions on the spray target.

Thus, according to the present exemplary embodiment, ion spraying apparatus 100 flies, detects the spray target, moves to the location of the spray target, and then sprays ions. This allows ion spraying apparatus 100 to spray ions on the spray target from an optimal distance. As a result of this, it is possible to securely obtain effects including sterilization in the spray target.

According to the present exemplary embodiment, ion spraying apparatus 100 sprays ions on the spray target at a predetermined frequency, so that the effects including sterilization can last in the spray target without a person's awareness.

According to the present exemplary embodiment, therefore, it is possible to perform ion-spraying on the spray target from an optimal distance at a predetermined frequency, and to allow the effects of sterilization, disinfection, or deodorization to last in the spray target.

Second Exemplary Embodiment

Figure 4:
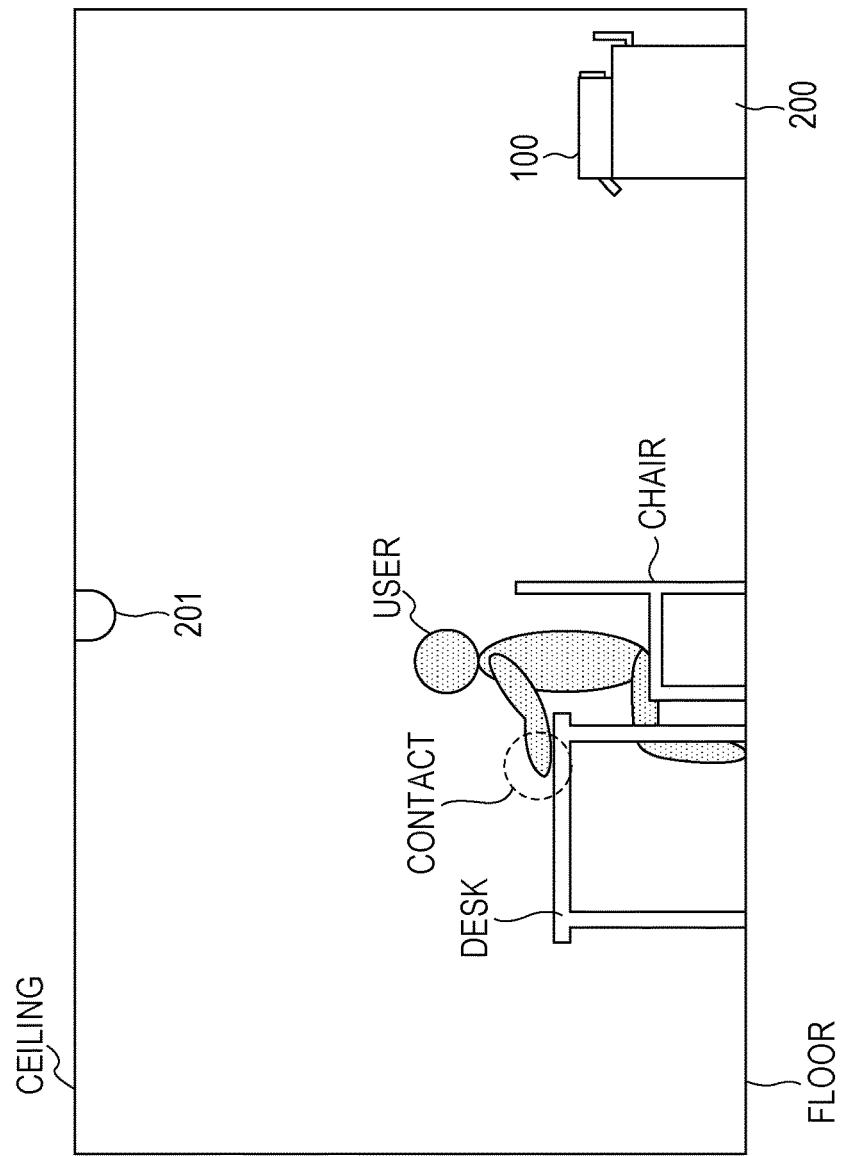
FIG. 4 is a diagram illustrating an example of a configuration of an ion spraying system according to a second exemplary embodiment of the present disclosure.

FIG. 4 illustrates an example of a configuration of an ion spraying system according to the present exemplary embodiment. The ion spraying system illustrated in FIG. 4 includes ion spraying apparatus 100 that sprays ions on spray targets, and control apparatus 200 that specifies the spray targets.

Control apparatus 200 illustrated in FIG. 4 includes a body, and camera 201 installed at a position (such as a ceiling or an air conditioner) at which camera 201 can monitor entire space where ion spraying apparatus 100 can fly. Control apparatus 200 is not limited to the configuration illustrated in FIG. 4. An apparatus into which functions of the body and the camera are integrated may be installed at a position similar to the position of camera 201 illustrated in FIG. 4.

Control apparatus 200 uses an image received from camera 201 to detect a motion of a person (or a part of the person) and to recognize objects the person contacts. For example, in FIG. 4, control apparatus 200 recognizes each of the objects (an upper surface of a desk in FIG. 4) that is contacted by a hand of a person, and stores a location of the recognized object. Control apparatus 200 then measures a number of contacts made by the person contacting the object, and determines a spray target to be sprayed with ions depending on the measured number of contacts. For example, control apparatus 200 determines an object that the person contacts many times as the spray target.

Examples of the objects to be contacted by a hand of a person may include a doorknob and a remote control, in addition to the desk illustrated in FIG. 4. Control apparatus 200 stores a latest location of the object that is movable to an unspecified position, such as a remote control.

Ion spraying apparatus 100 has a configuration similar to the configuration of ion spraying apparatus 100 illustrated in FIG. 1A, FIG. 1B, and FIG. 2. Ion spraying apparatus 100 receives spraying target information that specifies the spray targets from control apparatus 200. In a similar manner as in the first exemplary embodiment, ion spraying apparatus 100 flies toward each of the spray targets indicated by the received spraying target information, and sprays ions in a condition that ion spraying apparatus 100 is near the spray target.

[Configuration of Control Apparatus 200]

Figure 5:
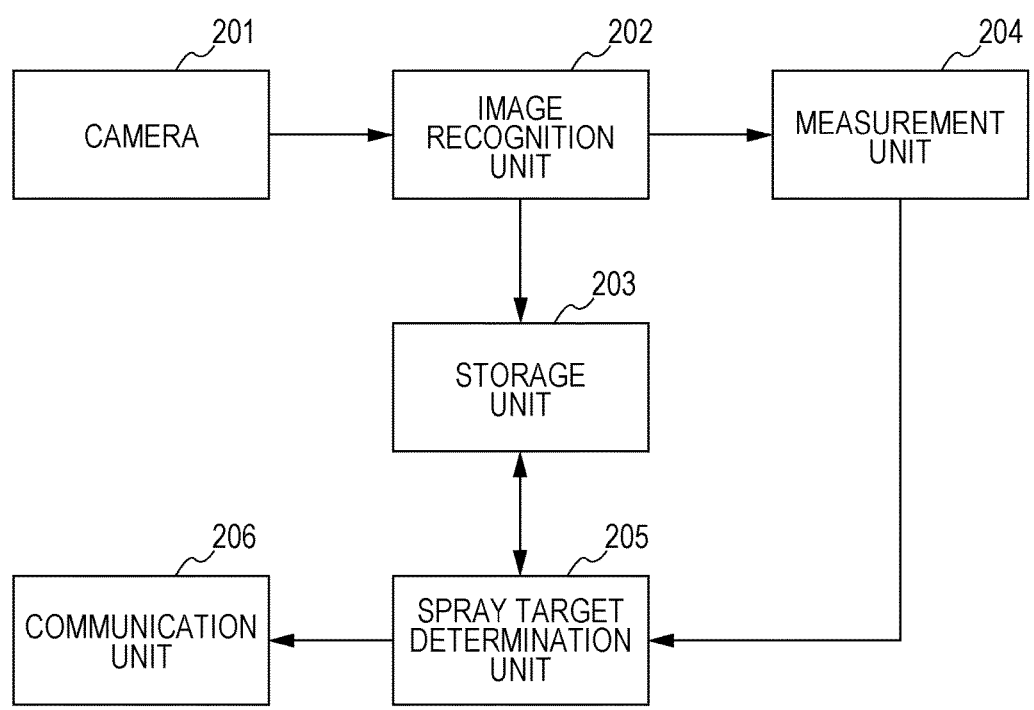
FIG. 5 is a block diagram illustrating a configuration of a control apparatus according to the second exemplary embodiment of the present disclosure.

FIG. 5 is a block diagram illustrating a configuration of control apparatus 200 according to the present exemplary embodiment. Control apparatus 200 includes camera 201, image recognition unit 202, storage unit 203, measurement unit 204, spraying target determination unit 205, and communication unit 206.

Camera 201 outputs the captured image to image recognition unit 202, as described above.

Image recognition unit 202 applies image recognition processing to the image received from camera 201, detects a motion of a person, and recognizes the objects contacted by the person. Image recognition unit 202 outputs the spraying target information (such as a location and image of each of the objects) regarding the recognized objects to storage unit 203 and measurement unit 204.

Storage unit 203 stores information regarding the object contacted by the person, the information being received from image recognition unit 202. Storage unit 203 outputs the stored information regarding the objects to spraying target determination unit 205 in response to a request from spraying target determination unit 205.

Measurement unit 204 measures the number of contacts made by the person for each object that is received from image recognition unit 202 (the object recognized by image recognition unit 202). For example, measurement unit 204 may measure the number (frequency) of contacts made by the person in a predetermined time period (for example, one day). Measurement unit 204 outputs a measurement result of the number of contacts that the person makes with each object to spraying target determination unit 205.

Spraying target determination unit 205 determines the spray targets to be sprayed with ions from among the objects recognized by image recognition unit 202 based on the measurement result (the number of contacts) received from measurement unit 204. For example, spraying target determination unit 205 may determine each of the objects having the measured number of contacts that is a predetermined larger number from among the objects recognized by image recognition unit 202 as the spray target. Spraying target determination unit 205 may determine the object having the measured number of contacts that is larger than a predetermined number from among the objects recognized by image recognition unit 202 as the spray target. Spraying target determination unit 205 acquires information that specifies the determined spray target from storage unit 203 to generate the spraying target information. Spraying target determination unit 205 outputs the generated spraying target information to communication unit 206.

Communication unit 206 sends the spraying target information (location information or image information) received from spraying target determination unit 205 to ion spraying apparatus 100.

Contact infection results from unconscious contact of a person with a specific substance in many cases. Therefore, specification of the spray target to be sprayed with ions provided by the person himself or herself is insufficient. In contrast, according to the present exemplary embodiment, control apparatus 200 determines the spray target based on the number of contacts made by the person with the object. That is, according to the present exemplary embodiment, control apparatus 200 automatically determines the object that is likely to cause contact infection, and allows ion spraying apparatus 100 to spray ions on the object determined by control apparatus 200.

In this way, the present exemplary embodiment provides effects including sterilization by ions in the object that the person makes unconscious contact, without the person's awareness. In addition, according to the present exemplary embodiment, ion spraying apparatus 100 can spray ions (close range) on the spray target from an optimal distance at a predetermined frequency, in a same manner as in the first exemplary embodiment. Thus, according to the present exemplary embodiment, it is possible to perform ion-spraying from the optimal distance on the spray target at a predetermined frequency, and to allow the effects of sterilization, disinfection, or deodorization to last in the spray target.

Image recognition unit 202 may be adapted to recognize a specific person who is previously registered in storage unit 203. This prevents, for example, an infant previously registered in storage unit 203 from licking an insanitary thing and upsetting health without parent's notice, by causing image recognition unit 202 to recognize an object that the infant often contacts by the mouth and causing ion spraying apparatus 100 to disinfect such an object at a high frequency.

Measurement unit 204 may measure the number of contacts during a predetermined time period. Measurement unit 204 may also measure a cumulative total of the number of contacts made by the person. For example, spraying target determination unit 205 may determine the object having the cumulative total of number of contacts that exceeds a predetermined number (threshold value) as the spray target. In this case, measurement unit 204 may reset (0 times) the cumulative number of contacts of the object that is determined as the spray target. This allows ion spraying apparatus 100 to spray ions every time the person contacts the object a predetermined number of times, and allows the effects including sterilization of the object to last.

Alternatively, spraying target determination unit 205 may reduce the predetermined number of times for determination as the spray target, as the cumulative number of contacts increases. This allows ion spraying apparatus 100 to spray ions on the object more frequently as the number of contacts with the person increases, and to adjust a degree of sterilization in accordance with a frequency of contact with the person.

Control apparatus 200 may acquire, from ion spraying apparatus 100, a three-dimensional map that shows a structure (locations of a ceiling, a wall, and a household utensil) of space (room) in which ion spraying apparatus 100 can fly. In this case, control apparatus 200 may store the location of the object contacted by the hand of the person in the acquired three-dimensional map, and may send location information about the object selected as the spray target in the three-dimensional map to ion spraying apparatus 100. Ion spraying apparatus 100 may detect, in the space, the spray target in the three-dimensional map, the spray target being indicated in the location information (spraying target information) received from control apparatus 200.

Although a description has been given of a case of using the image captured by camera 201 illustrated in FIG. 4 in the present exemplary embodiment, control apparatus 200 may use an image captured by ion spraying apparatus 100, instead of camera 201. That is, control apparatus 200 may use the image acquired from ion spraying apparatus 100 to recognize the object contacted by the person. This allows ion spraying apparatus 100 to move in the space, thereby reducing a blind spot during monitoring a motion of the person, as compared with fixed camera 201 illustrated in FIG. 4. For example, this allows ion spraying apparatus 100 to move to a location where a motion of the hand of the person can be captured to recognize the object contacted by the hand of the person. Moreover, according to the present exemplary embodiment, ion spraying apparatus 100 may include functions of control apparatus 200 illustrated in FIG. 5.

In the present disclosure, a function of detecting dust generated by the person may be added. Dust generation corresponds, for example, to a case of scattering bacteria when the person coughs, or to a case of stirring up dust that contains bacteria, pollen, and the like when the person performs intense exercise in a room. In the former case, a microphone may be newly installed on the ceiling like camera 201 to detect a sound having a pattern characteristic of a cough. In the latter case, camera 201 may detect that a motion of the person (speed, acceleration) has exceeded a certain threshold value.

The scattered bacteria and pollen may drift in the room for a while, and may then adhere to a place with which the person is likely to make contact. Accordingly, when an event of dust generation is detected, control apparatus 200 detects a location of dust generation with camera 201, extracts the object near the dust generation location from among the above-described spray targets, and sprays ions on the extracted object with priority. This allows sterilization and disinfection before the person makes contact with the newly scattered bacteria.

Control apparatus 200 may further include a dust generation detector that detects the event and location of dust generation. A person who performs the event of dust generation detected by the dust generation detector and a person who makes contact with the object may be a same person and may be separate persons.

Spraying target determination unit 205 may determine the object that is around the location where dust generation is detected as the high-priority spray target to be sprayed with ions from among the spray targets to be sprayed with ions specified by the spraying target information. Spraying target determination unit 205 may generate priority information including information that specifies the high-priority spray target to be sprayed with ions.

Communication unit 206 may send the priority information to ion spraying apparatus 100.

Communication unit 101 may receive the priority information from control apparatus 200.

Spraying target detector 104 may detect, with priority, the high-priority spray target to be sprayed with ions specified by the priority information from among the spray targets to be sprayed with ions specified by the spraying target information.

Spraying target detector 104 may acquire, with priority, location information about the high-priority spray target to be sprayed with ions specified by the priority information from among the spray targets to be sprayed with ions specified by the spraying target information.

Spray control unit 102 may determine, with priority, a moving direction to the high-priority spray target to be sprayed with ions specified by the priority information from among the spray targets to be sprayed with ions specified by the spraying target information, based on the location information about the high-priority spray target to be sprayed with ions specified by the priority information.

When a distance between the high-priority spray target to be sprayed with ions specified by the priority information, and the ion spraying apparatus is within a threshold value, spray control unit 102 may perform, with priority, ion-spraying on the high-priority spray target to be sprayed with ions, from among the spray targets to be sprayed with ions specified by the spraying target information.

Flight control unit 106 may control, with priority, a flight of ion spraying apparatus 100 in the moving direction to the high-priority spray target to be sprayed with ions specified by the priority information from among the spray targets to be sprayed with ions specified by the spraying target information.

Each of the exemplary embodiments of the present disclosure has been described above.

In each of the exemplary embodiments described above, a description has been given of a case where ion spraying apparatus 100 (FIG. 1) is a small helicopter-shaped apparatus that has propellers. However, a flight device included in ion spraying apparatus 100 is not limited to propellers, and ion spraying apparatus 100 may be an airship that has a balloon, for example.

According to the present exemplary embodiment, ion spraying apparatus 100 may previously exclude objects on which ions are preferably not sprayed, from the spray targets. Examples of the objects to be excluded from the spray targets may include a handmade fermented-soybeans incubator with which a person may make contact. This is because *Bacillus* natto contained in the handmade fermented-soybeans incubator will become extinct when ions are sprayed on *Bacillus* natto. For example, ion spraying apparatus 100 may previously register the objects to be excluded from the spray targets, and may affix, on each of the objects to be excluded, a marker that allows ion spraying apparatus 100 to recognize that the object is to be excluded. In addition, ion spraying apparatus 100 may send information about the recognized spray target to a device appliance retained by a person, and the person may select whether to exclude the spray target. That is, ion spraying apparatus 100 sprays ions on the spray target when the detected spray target is not set as the object to be excluded from ion-spraying. This allows ion spraying apparatus 100 to spray ions on the objects that need an operation such as sterilization.

According to each of the exemplary embodiments, ion spraying apparatus 100 or control apparatus 200 may operate to spray ions on the spray target when, for example, no person is present in a vicinity of the spray target. This prevents ion spraying apparatus 100 from spraying ions by mistake on a person who is near the spray target.

According to each of the above exemplary embodiments, what ion spraying apparatus 100 sprays is not limited to microparticle ions, such as nanoe, and may be anything aimed at sterilization, disinfection, or deodorization.

In each of the exemplary embodiments described above, a description has been given of a case where the present disclosure is implemented by hardware as an example, but the present disclosure can also be implemented by software in cooperation with hardware.

Each of functional blocks (FIG. 2, FIG. 5) used for the description of each of the above exemplary embodiments is typically implemented as an LSI (Large-Scale Integration) circuit that is an integrated circuit. These functional blocks may be formed as separate chips, or some or all of the functional blocks may be included in one chip. Although the integrated circuit is called LSI here, the integrated circuit may be referred to as an IC, a system LSI, a super LSI, and an ultra LSI, depending on a difference in a degree of integration.

Methods for circuit integration are not limited to LSI, and may be implemented by using a dedicated circuit or a general-purpose processor. Circuit integration may use an FPGA (Field Programmable Gate Array) that is programmable after manufacture of an LSI, or a reconfigurable processor in which connections or settings of circuit cells within the LSI are reconfigurable.

Furthermore, if an advance in a semiconductor technology or another related technology yields a circuit integration technology that may substitute for LSI, the functional blocks may be obviously integrated by using such a technology. Biotechnology may be applied.

An overview of one aspect of the present disclosure is as follows.

An ion spraying apparatus according to one aspect of the present disclosure includes: a receiver unit that receives spraying target information indicating a spray target; a spraying target detector that detects the spray target; a spray controller that has the ion spraying apparatus move toward the detected spray target and performs ion-spraying when a distance between the spray target and the ion spraying apparatus is within a first threshold value; and a flight controller that controls a flight of the ion spraying apparatus.

The spray controller may perform the ion-spraying when a person is not present in a vicinity of the detected spray target.

The spray controller may perform the ion-spraying when the detected spray target is not set as an object to be excluded from the ion-spraying.

The spraying target information may be one of image information that indicates the spray target, and location information that indicates a location of the spray target.

An ion spraying system according to one aspect of the present disclosure includes an ion spraying apparatus and a control apparatus, wherein the control apparatus includes: a recognition unit that recognizes objects contacted by a person; a measurement unit that measures a number of contacts made by the person for each of the recognized objects; a spraying target determination unit that determines a spray target that is an object on which the ion spraying apparatus performs ion-spraying from among the recognized objects based on the measured number of contacts, and generates spraying target information that specifies the spray target; and a first communication unit that sends the spraying target information to the ion spraying apparatus, wherein the ion spraying apparatus includes: a second communication unit that receives the spraying target information from the control apparatus; a spraying target detector that detects the spray target indicated by the spraying target information; a spray control unit that determines a moving direction of the ion spraying apparatus based on location information on the detected spray target, and performs ion-spraying when a distance between the spray target and the ion spraying apparatus is within a first threshold value; and a flight control unit that controls a flight of the ion spraying apparatus.

The spraying target determination unit may determine an object having the measured number of contacts that exceeds a second threshold value during a predetermined time period as the spray target.

The recognition unit may recognize a registered specific person in advance, and may recognize an object contacted by the specific person.

The spraying target information may be one of image information that indicates the spray target and location information that indicates a location of the spray target.

The control apparatus may further include a dust generation detector that detects an event and location of dust generation. The spraying target determination unit may determine, from among the spray targets, an object that is around the location where the event of the dust generation is detected as the high-priority spray target. The spraying target determination unit may generate priority information including information that specifies the high-priority spray target. The first communication unit may send the priority information to the ion spraying apparatus. The second communication unit may receive the priority information from the control apparatus. The spraying target detector may detect, with priority, the high-priority spray target specified by the priority information from among the spray targets specified by the spraying target information.

An ion spraying method according to one aspect of the present disclosure includes: receiving spraying target information that specifies a spray target; detecting location information on the spray target indicated in the spraying target information; determining a moving direction of an ion spraying apparatus to the detected spray target based on the location information on the detected spray target; controlling a flight of the ion spraying apparatus; and spraying ions on the spray target when a distance between the spray target and the ion spraying apparatus is within a first threshold value.

The present disclosure is useful in the ion spraying device or the like that sprays ions on the spray target toward which the device flies and approaches.

What is claimed is:
1. An ion spraying system comprising:
an ion spraying apparatus; and
a control apparatus,
wherein the control apparatus comprises:
a camera configured to
capture an image,
recognize objects contacted by a person based on the image captured by the camera of the control apparatus, and
measure a number of contacts made by the person for each of the recognized objects based on the image captured by the camera of the control apparatus;
a processor configured to determine a spray target that is an object on which the ion spraying apparatus is to perform ion-spraying from among the recognized objects based on the measured number of contacts, and generate spraying target information that specifies the spray target; and
a transmitter configured to transmit the spraying target information to a receiver of the ion spraying apparatus,
wherein the ion spraying apparatus comprises:
the receiver configured to receive the spraying target information from the transmitter of the control apparatus;
a camera configured to capture an image and detect the spray target indicated in the spraying target information based on the image captured by the camera of the ion spraying apparatus;
a plurality of propellers configured to cause flight of the ion spraying apparatus;
a processor configured to control the flight of the ion spraying apparatus, determine a moving direction of the ion spraying apparatus based on location information on the detected spray target, and control the ion spraying apparatus to perform ion-spraying when a distance between the spray target and the ion spraying apparatus is determined to be within a first threshold value.

2. The ion spraying system according to claim 1, wherein the processor of the control apparatus is further configured to determine, based on information provided by the camera of the control apparatus, an object having the measured number of contacts that exceeds a second threshold value during a predetermined time period as the spray target.

3. The ion spraying system according to claim 1, wherein the camera of the control apparatus is further configured to recognize a registered specific person in advance, and recognize an object contacted by the registered specific person.

4. The ion spraying system according to claim 1, wherein the transmitter of the control apparatus is further configured to transmit image information, included in the spraying target information, that indicates the spray target and location information that indicates a location of the spray target.

5. The ion spraying system according to claim 1, wherein
the control apparatus further comprises a dust detector configured to detect an event and a location of dust generation,
the processor of the control apparatus is further configured to determine as high priority spray targets, from among the spray targets, each of the objects that is around the location where the event of the dust generation is detected, and generate priority information including information indicating priority of the high priority spray targets,
the transmitter of the control apparatus is further configured to transmit the priority information to the receiver of the ion spraying apparatus,
the receiver of the ion spraying apparatus is further configured to receive the priority information from the transmitter of the control apparatus, and
the camera of the ion spraying apparatus is further configured to detect with priority, from among the spray targets specified by the spraying target information, each of the high priority spray targets specified by the priority information.

* * * * *